United States Patent [19]

Vinick

[11] 4,359,416

[45] Nov. 16, 1982

[54] PROCESS FOR PREPARING L-CARNOSINE

[75] Inventor: Fredric J. Vinick, Waterford, Conn.

[73] Assignee: Pfizer Inc., New York, N.Y.

[21] Appl. No.: 282,366

[22] Filed: Jul. 13, 1981

[51] Int. Cl.$^3$ ............................................. C07C 103/52
[52] U.S. Cl. ................................ 260/112.5 R; 548/344
[58] Field of Search .................... 548/344; 260/112.5 R

[56] References Cited

U.S. PATENT DOCUMENTS 3,846,398  11/1974  Hirschmann et al. ............ 260/112.5

OTHER PUBLICATIONS

*Chemical Abstracts,* 89:432832 (1978) [Vladzimirskaya, E., et al., Tezisy Dokl. Navchn. Sess. Khim. Tekhnol. Org. Soedin. Serv. Sernistykh Neftei, 14th 1975, 204–205].

*Primary Examiner*—Richard A. Schwartz
*Attorney, Agent, or Firm*—Charles J. Knuth; Albert E. Frost; James M. McManus

[57] ABSTRACT

Process for preparing L-carnosine by reacting L-histidine and tetrahydro-1,3-thiazin-2,4-dione in an aqueous medium at a selected pH and temperature range followed by removal of carbon oxysulfide at acid pH, removal of water and crystallization of product wherein pH adjustments are made with substituted ammonium hydroxides and organic acids having pKa $\leq 3.75$.

7 Claims, No Drawings

PROCESS FOR PREPARING L-CARNOSINE

BACKGROUND OF THE INVENTION

1. Field of the Invention

This invention relates to a process for the synthesis of a natural peptide having medicinal uses. In particular, this invention concerns a process for the preparation of L-carnosine, beta-alanyl-L-histidine.

2. Description of the Art

L-Carnosine, beta-alanyl-L-histidine, is a natural occurring dipeptide which is found in vertebrate skeletal muscle and in the olfactory bulbs and nasal tissue of animals. Recently it has been shown in a review by K. Nagai and T. Yamane [Heterocycles, 10, 277 (1978)] that L-carnosine possesses the remarkable property of accelerating wound healing particularly when used following oral surgical procedures [K. Nagai, et al., *J. Nihon Univ. Sch. Dent.*, 16, 29 (1974)].

L-Carnosine has been synthesized by (1) the reaction of L-histidine with beta-iodopropionyl chloride followed by treatment with ammonia [L. Baumann, et al., *J. Biol. Chem.*, 35, 263 (1918)]; (2) reaction of beta-carbobenzoxypropionyl azide with L-histidine methyl ester followed by ester hydrolysis and deblocking [R. Sifferd, et al., *J. Biol. Chem.*, 108, 753 (1935)]; (3) reaction of beta-phthaloylalanyl chloride with L-histidine followed by removal of the phthaloyl group [R. Turner, *J. Am. Chem. Soc.*, 75, 2388 (1953) and G. Losse, et al., *Chem. Ber.* 94, 2768 (1961)]; (4) reaction of L-histidine and a mixed anhydride of beta-phthaloylalanyl followed by removal of the phthaloyl group [H. Rinderknecht, et al., *J. Org. Chem.*, 229, 1968 (1964)]; (5) acylation of L-histidine methyl ester with beta-phthaloylalanine p-nitrophenyl ester followed by removal of the phthaloyl group [A. A. Glemzha, et al., *Izo. Akad. Nauk. USSR*, Ser. Khim, 861 (1966)]; and (6) reaction of carbobenzoxybeta-alanine p-nitrophenyl ester with L-histidine followed by removal of the blocking group [C. Pinelli, et al., *Il Farmico, Ed. Sci.*, 23, 859 (1968)].

Recently, U.S. Pat. No. 3,846,398 reported the synthesis of peptides of alpha-amino acids using a substituted thiazolid-2,5-dione, in which the pH control was adjusted with inorganic acids and an alkali metal hydroxide.

SUMMARY OF THE INVENTION

It has now been discovered that L-carnosine can be prepared in a simple reaction which comprises the steps of reacting L-histidine with tetrahydro-1,3-thiazin-2,4-dione in an aqueous medium at a pH of from about 8.5 to 9.5 and at a temperature of from about 0° to about 25° C.; dethiocarboxylating by acidifying to a pH of below about 4.5; adjusting to a pH of 8.2; removing the water; and separating the product from the residue by crystallizing from an alkanol of one to four carbon atoms, a polychlorinated hydrocarbon of one to two carbon atoms or an alkyl acetate of three to six carbon atoms, with the proviso that pH adjustments above 7.0 are made with a tetraalkylammonium or trialkylbenzylammonium hydroxide wherein said alkyl contains one to four carbon atoms and pH adjustments below 7.0 are made with an organic acid having a pKa ≦3.75.

Preferred features of the present process are a reaction temperature of about 5° C., removal of the water under vacuum at about 45° C., adjustment of the pH above 7.0 with tetraethylammonium hydroxide, adjustment of the pH below 7.0 with formic acid and crystallizing the product from ethanol.

Additional preferred features of the present process are a reaction temperature of about 5° C., removal of the water under vacuum at about 45° C., adjustment of the pH above 7.0 with tetra-n-butylammonium hydroxide, adjustment of pH below 7.0 with methanesulfonic acid and crystallizing the product from ethanol.

The present process, as opposed to those methods for preparing L-carnosine in the literature, can be carried out in one reaction vessel, does not require the removal of blocking groups and gives the desired product in excellent yields.

A feature of many synthetic methods for preparing peptides reported in the literature is the use of inorganic acids and alkali metal or alkaline earth metal hydroxides for adjustment of pH. In instances when the peptide formed is relatively insoluble in an aqueous medium, separation of said peptide from salts resulting from the neutralization of inorganic acids and alkali metal or alkaline earth metal hydroxides is usually not a serious problem. However, in the case of L-carnosine, which has a water solubility of 1 g. in 3.1 ml. of water (25° C.), it is difficult to separate said salts from the desired product without extensive laboratory manipulations. The use of bases selected from tetraalkyl- and trialkylbenzylammonium hydroxides and organic acids having a pKa of ≦3.75, as in the presently claimed process, gives rise to salts which, unlike salts from inorganic acids and alkali metal or alkaline earth metal hydroxides, are soluble in alkanols of one to four carbon atoms, polychlorinated hydrocarbons of one to two carbon atoms and alkyl acetates of three to six carbon atoms, solvents in which L-carnosine has very low solubility.

DETAILED DESCRIPTION OF THE INVENTION

L-Carnosine is readily synthesized in a one step chemical reaction of L-histidine and tetrahydro-1,3-thiazin-2,4-dione in an aqueous medium at a pH of about 8.5 to about 9.5 depicted as follows:

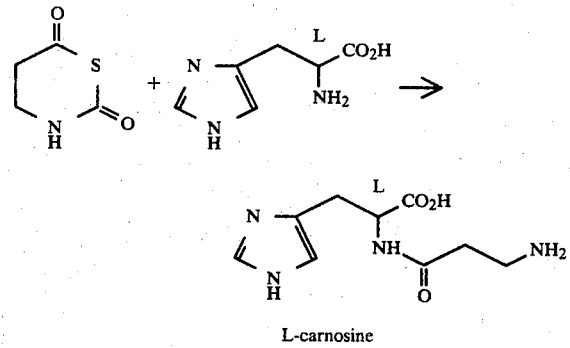

L-carnosine

In practice, a suspension of L-histidine in water is treated with sufficient amounts of a tetraalkyl- or trialkylbenzylammonium hydroxide in water to give a pH of about 8.5 to about 9.5. To the resulting solution is added tetrahydro-1,3-thiazin-2,4-dione. The pH, which starts to decrease as the reaction proceeds is adjusted to the range of about 8.5 to about 9.5 by the addition of more of the aforementioned bases. After approximately 15 minutes the pH stabilizes and ceases to fall.

Reaction temperature is not critical, but elevated temperatures somewhat above 25° C. leads to decomposition of one of the starting reagents, tetrahydro-1,3-thiazin-2,4-dione. Temperatures below 0° C. slow the reaction unnecessarily and offer no practical advantages. Accordingly, a reaction temperature range of about 0° C. to about 25° C. is operable, with a preferred temperature of about 5° C.

Employing a reaction temperature of about 5° C. the reaction is generally complete in about 15-20 minutes. To ensure completeness in the reaction the mixture is usually allowed to stir at the reaction temperature for about one hour.

Although the reaction to form L-carnosine requires equimolar amounts of L-histidine and tetrahydro-1,3-thiazin-2,4-dione it is preferred that an excess of the latter reagent be employed. Accordingly, a 100-200% excess of the requisite reagent provides excellent yields of the desired product without any loss of quality.

Following the reaction of the starting reagents, the pH is adjusted below about 4.5 in order to allow for the dethiocarboxylating, or loss of carbon oxysulfide, from the reaction mixture. The preferred pH range for this dethiocarboxylation is 4.4-4.0. The pH adjustment is effected using an organic acid having a pKa of $\leq 3.75$, which is the pKa of formic acid.

In addition to formic acid, there are wide variety of organic acids which meet this criteria, including an alkanesulfonic acid, such as methanesulfonic acid, an arylsulfonic acid, such as benzene-or p-toluenesulfonic acid, certain benzoic acids, such as o, m and p-nitrobenzoic acids, and salicylic acid, and certain dibasic acids such as oxalic and malonic acids. In addition to having the requisite pKa, the organic acid employed must also be inert in its reaction with either the starting reagents or the final product of the claimed process. The preferred acids for adjustment of pH below 7.0 are formic acid and methanesulfonic acid.

After the gas evolution has ceased, the pH is adjusted to 8.2, the isoelectric point for L-carnosine, and the water removed from the reaction mixture. This removal can be effected by a variety of methods such as evaporation at room temperature, freeze drying, removal in vacuo, etc. The preferred method for removal is under vacuum at about 45° C., an efficient and rapid technique.

The residue remaining after the water has been removed contains the desired product, L-carnosine, certain by-products and salts resulting from neutralization of acids and bases in adjusting the pH. By the selection of the aformentioned bases and acids the salts formed have appreciable solubility in certain solvents. By proper selection it is possible to choose a solvent which will solubilize the salts resulting from pH adjustments as well as certain byproducts formed in the reaction, but which will not solubilize the final product. Such solvents include alkanols of one to four carbon atoms, such as methanol and ethanol; polychlorinated hydrocarbons of one to two carbon atoms such as chloroform; and alkyl acetates of three to six carbon atoms such as ethyl acetate.

On treatment of the residue with absolute ethanol all the material initially dissolves, followed by the slow crystallization of L-carnosine. In general, several hours are required for the crystallization process to be complete. The product thus isolated is of high quality, and is obtained in high yields.

As previously indicated, L-carnosine is a natural peptide having medicinal use, in particular, it possesses the property of accelerating wound healing particularly when used following oral surgical procedures. The use of L-carnosine for such treatment is described in the literature, in particular, by Nagai, et al., Heterocycles, 10, 277 (1978).

The following examples are provided solely for the purpose of further illustration.

EXAMPLE 1

To a stirred suspension of 6.20 g. (40 mmol) of L-histidine in 60 ml. of water at 0°-10° C. was added sufficient 20% aqueous tetraethylammonium hydroxide to give a pH of about 9.2. To the resulting solution was added portionwise 10.5 g. (80 mmol) of tetrahydro-1,3-thiazin-2,4-dione with vigorous stirring, the pH being maintained at about 8.5-9.2 by the addition of 20% aqueous tetraethylammonium hydroxide as needed. After completion of the addition the reaction mixture was allowed to stir for one hour, and was then treated with sufficient 98% formic acid to give a pH of about 4.4. When the gas evolution ceased ($\sim$5 minutes) the pH was adjusted to 8.2 with 20% aqueous tetraethylammonium hydroxide, and the water removed in vacuo at 45°-50° C. The residual clear oil was stirred with 600 ml. of absolute ethanol at room temperature. Fine white crystals of L-carnosine slowly separated from the solution over a period of several hours. The product was filtered, washed successively with 95% ethanol, methylene chloride, 95% ethanol, methylene chloride, 95% ethanol and ether, and was then dried, 7.2 g. (79.6% yield), m.p. 262° C. (dec.), previously reported [*Biochem. Preparations*, 4, 38 (1955) m.p. 260° C. (dec.)].

The NMR spectrum (D$_2$O) showed absorption at 2.64 (t, 2H, J=6 Hz), 3.04 (AB of ABX, 2H, $J_{AB}$=16 Hz), 3.20 (t, 2H, J=6 Hz), 4.44 (X of ABX, 1H, $J_{AX}+J_{BX}$=14 Hz), 6.94 (s, 1H) and 7.70 (s, 1H) ppm.

EXAMPLE 2

L-Histidine (1.55 g., 10 mmol) was stirred as a suspension in 15 ml. of water at 0°-10° C. and the pH adjusted to about 9.0 with 40% methanolic benzyltrimethylammonium hydroxide. Tetrahydro-1,3-thiazin-2,4-dione (2.62 g., 20 mmol) was added portionwise with vigorous stirring, the pH being maintained at about 8.5-9.5 by the addition of 40% methanolic benzyltrimethylammonium hydroxide as needed. After stirring for one hour, the pH was adjusted to 4.4 with 98% formic acid, and the carbon oxysulfide gas allowed to escape. When gas evolution ceased ($\sim$5 minutes), the pH was adjusted to 8.2 with 40% methanolic benzyltrimethylammonium hydroxide, and the water removed from the reaction mixture in vacuo at room temperature. The solution, resulting from dissolving the residue in 150 ml. of absolute ethanol, gradually precipitated by product, L-carnosine, over a period of several hours. The product was filtered, washed with absolute ethanol and dried, 1.46 g. (64.6% yield). The product was identical to that of Example 1.

EXAMPLE 3

L-Histidine (1.55 g., 10 mmol) was stirred as a suspension in 15 ml. of water at 0°-10° C. and the pH adjusted to about 9.0 with 20% aqueous tetramethylammonium hydroxide solution. Tetrahydro-1,3-thiazin-2,4-dione (2.62 g., 20 mmol) was then added portionwise with vigorous stirring, the pH being maintained at 8.5-9.5 by the addition of 20% aqueous tetramethylammonium hydroxide solution as needed. After completion of the tetrahydro-1,3-thiazin-2,4-dione addition, the reaction mixture was allowed to stir for one hour. The pH was then lowered to about 4.4 with 98% formic acid, and the carbon oxysulfide allowed to evolve over a period of about 5 minutes. The pH was then raised to 8.2 with 20% aqueous tetramethylammonium hydroxide solution and the reaction mixture concentrated to dryness in vacuo. The clear oil residue was dissolved in 150 ml. of absolute ethanol and allowed to stir slowly. The L-carnosine which precipitated was filtered, washed with absolute ethanol and dried, 1.40 g. (61.9% yield). The sample was indistinguishable from that isolated in Example 1.

EXAMPLE 4

Starting with 1.55 g. (10 mmol) of L-histidine, 2.62 g. (20 mmol) of tetrahydro-1,3-thiazin-2,4-dione, 20% aqueous tetramethylammonium hydroxide solution to raise the pH and methanesulfonic acid to lower the pH, and following the procedure of Example 1, there was isolated 1.13 g. (50% yield) of L-carnosine.

EXAMPLE 5

L-Histidine (1.55 g., 10 mmol) and tetrahydro-1,3-thiazin-2,4-dione (2.62 g., 20 mmol) were reacted according to the procedure of Example 1, basic pH control being effected with 40% aqueous tetra-n-butylammonium hydroxide and acid pH control with 98% formic acid. The isolated yield of L-carnosine was 1.52 g. (67.3% yield).

EXAMPLE 6

Following the procedure of Example 1., 1.55 g. (10 mmol) of L-histidine and 2.62 g. (20 mmol) of tetrahydro-1,3-thiazin-2,4-dione were reacted, using 40% aqueous tetra-n-butylammonium hydroxide solution to raise pH and methanesulfonic acid to lower pH, to give 1.80 g. (79.6% yield) of L-carnosine.

EXAMPLE 7

Starting with 1.55 g. (10 mmol) of L-histidine, 2.62 g. (20 mmol) of tetrahydro-1,3-thiazin-2,4-dione, 40% methanolic benzyltri-n-butylammonium hydroxide solution to raise the pH benzenesulfonic acid to lower the pH and ethyl acetate as the crystallizing solvent, and following the procedure of Example 1, there is isolated L-carnosine in good yield.

EXAMPLE 8

L-Histidine (1.55 g., 10 mmol) and tetrahydro-1,3-thiazin-2,4-dione (2.62 g., 20 mmol) are reacted according to the procedure of Example 1, basic pH control being effected with 40% aqueous tetra-n-propylammonium hydroxide and acid pH control with butanesulfonic acid, to give the desired product in good yield.

EXAMPLE 9

Following the procedure of Example 1, 1.55 g. (10 mmol) of L-histidine and 2.62 g. (20 mmol) of tetrahydro-1,3-thiazin-2,4-dione are reacted, using 40% aqueous tetramethylammonium hydroxide solution to raise pH and m-nitrobenzoic acid to lower pH, to give L-carnosine in good yield.

I claim:

1. A process for preparing L-carnosine which comprises the steps of reacting L-histidine with tetrahydro-1,3-thiazin-2,4-dione in an aqueous medium at a pH of from about 8.5 to about 9.5 and at a temperature of from about 0° to about 25° C.; dethiocarboxylating by acidifying to a pH of below about 4.5; adjusting to a pH of 8.2; removing the water; and separating the product from the residue by crystallizing from a solvent selected from the group consisting of alkanols having one to four carbon atoms, polychlorinated hydrocarbons having one to two carbon atoms and alkyl acetates having three to six carbon atoms, with the proviso that pH adjustments above 7.0 are made with a base selected from the group consisting of trialkylbenzylammonium hydroxide and a tetraalkylammonium hydroxide wherein said alkyl contains from one to four carbon atoms and pH adjustments below 7.0 are made with an organic acid having a pKa $\leq 3.75$.

2. The process of claim 1 wherein the reaction temperature is about 5° C. and the crystallizing solvent is an alkanol having one to four carbon atoms.

3. The process of claim 2 wherein the water is removed under vacuum at about 45° C. and the crystallizing solvent is ethanol.

4. The process of claim 3 wherein pH adjustments above 7.0 are made with tetraethylammonium hydroxide and pH adjustments below 7.0 are made with an organic acid having a pKa of $\leq 3.75$.

5. The process of claim 4 wherein said organic acid is formic acid.

6. The process of claim 3 wherein pH adjustments above 7.0 are made with tetra-n-butylammonium hydroxide and pH adjustments below 7 are made with an organic acid having a pKa of $\leq 3.75$.

7. The process of claim 6 wherein said organic acid is methanesulfonic acid.

* * * * *